United States Patent
Malmagro

(12)
(10) Patent No.: US 6,413,498 B1
(45) Date of Patent: Jul. 2, 2002

(54) REMINERALIZING MATERIAL FOR ORGANOMINERAL TISSUES

(75) Inventor: Manuel Valiente Malmagro, Sant Cugat del Valles (ES)

(73) Assignee: Sociedad Limitado para el Desarrollo Cientificio Applicado, Barcelona (ES)

( * ) Notice: Subject to any disclaimer, the term of this patent is extended or adjusted under 35 U.S.C. 154(b) by 0 days.

(21) Appl. No.: 09/347,966

(22) Filed: Jul. 6, 1999

(51) Int. Cl.⁷ ................................................. A61K 7/16
(52) U.S. Cl. ......................................................... 424/49
(58) Field of Search ..................... 424/49–88

(56) References Cited

U.S. PATENT DOCUMENTS

| | | | | |
|---|---|---|---|---|
| 3,425,790 A | * | 2/1969 | Sloan ................................ 21/2 |
| 3,978,206 A | * | 8/1976 | Naumann et al. .............. 424/49 |
| 4,006,214 A | * | 2/1977 | Moser et al. ................. 423/112 |
| 4,080,440 A | * | 3/1978 | DiGiulio ....................... 424/49 |
| 4,083,955 A | * | 4/1978 | Grabenstetter et al. ........ 424/49 |
| 4,135,935 A | * | 1/1979 | Pfeil et al. ..................... 106/35 |
| 4,198,295 A | * | 4/1980 | Vajna .......................... 210/23 |
| 4,643,735 A | * | 2/1987 | Hayes et al. .................. 613/16 |
| 4,988,358 A | * | 1/1991 | Eppley et al. ................. 623/16 |
| 5,092,883 A | * | 3/1992 | Eppley et al. ................. 623/11 |
| 5,900,146 A | * | 5/1999 | Ballard et al. ............... 210/222 |
| 5,958,817 A | * | 9/1999 | Leavitt ......................... 502/64 |

FOREIGN PATENT DOCUMENTS

| | | | |
|---|---|---|---|
| EP | 265 186 | * | 4/1998 |
| FR | 2 719 996 | * | 11/1995 |
| GB | 1 477 899 | * | 6/1993 |
| RU | 18 11399 | * | 4/1993 |
| RU | 18 26976 | * | 7/1993 |
| SU | 825 074 | * | 5/1981 |
| WO | 98/30 191 | * | 7/1998 |

OTHER PUBLICATIONS

US PTO Translation of Zvonnikova (1986) Stomatologiya (Moscow) 65(3):20–22, Oct. 2000.*
US PTO Translation of Volozhin et al (1988) Stomatologiya (Moscow) 67(3):16–19, Oct. 2000.*
Zvonnikova, L. V. Stomatologiya (Moscow) 65/3): 20–22 Determination of the Elemental Composition of Monkey Tooth Dentin Using a Microprobe After Filling Large Cavities With Different Materials, 1986.*
Volozhin et al (Zvonnika, LV–Applicant) Stomatologiya (Moscow) 67(3)16–9 Experimental Substantiation and Clincal Use of Ion–Exchange Resin For Treatment of Deep Cavities.*
Muraviev et al (Valiknte, M Co–Applicants) Solvent Extrionech. 18(2). 345–374 Kinetics of Release of Calcium And Fluoride Ions From Ion–Exchange Resins In Artifical Saliva.*

* cited by examiner

Primary Examiner—Shep K. Rose
(74) Attorney, Agent, or Firm—Steinberg & Raskin, P.C.

(57) ABSTRACT

Together with other accessory products, includes a mixture of ion-exchange resins, cationic and anionic, charged with $Ca^{2+}$, $F^-$ and $PO_4^{3-}$ ions, in an approximate molar ratio of 2:1:1, respectively. Particularly preferred is a material in which the resins also have a charge of $Zn^{2+}$ ions representing a proportion of less than 1%, preferably close to 0.2% of the dry weight of the resin. The preferred resins are those whose base is cross-linked polystyrene with 2–14% divinylbenzene. The material is useful as first filler in the treatment of caries, especially deep caries, leading to remineralization of the dentin with a composition very close to the original composition, together with high microhardness. It is also useful as a component of dentifrice products such as pastes, elixirs and dental floss.

21 Claims, No Drawings

REMINERALIZING MATERIAL FOR ORGANOMINERAL TISSUES

FIELD OF THE INVENTION

The present invention relates to a material which, when placed in contact with a tooth or other human or animal organomineral tissue, leads to remineralization of said tissue (dentin in the case of the tooth) The invention is especially useful for combating caries and other dental problems.

BACKGROUND OF THE INVENTION

It is known that the development of caries can be partially restricted or inhibited by increasing the concentration of certain ions, especially fluoride, phosphate, calcium or, to a lesser extent, zinc ions. That is why some of these components are added in the form of water-soluble salts to drinking water, tooth pastes, elixirs for mouth rinses, etc. The positive effects of these salts are generally associated with their abrasive action or with their anti-microbial action.

The combined utilisation of said salts frequently gives rise to problems of incompatibility, such as the precipitation of insoluble products (e.g. calcium fluoride). In order to resolve the problem of chemical incompatibility, U.S. Pat. No. 3,978,206 (equivalent to DE 1.818.044) proposed the administration of ions by means of their release using carrier resins. But that patent considered solely the utilisation of resins carrying one type of ions: fluoride, phosphate or calcium, separately. And although in principle the disclosure of that patent does not exclude several ions being used in combination, nothing is said about the desirability of using a specific relative proportion of the ions.

Since it is known that caries and other dental problems are due to a demineralization of the components of the dentin (dental tissue), one possible channel of treatment lies in achieving the opposite effect, that is, partial remineralization of said components, which can lead to regeneration of the said dentin. But no suitable method is yet known in the art for obtaining this remineralization effect.

Furthermore, the current treatment of so-called deep caries (caries in which the bottom of the cavity reaches down very close to the upper end of the pulp containing the nerve) presents serious problems. One is associated with the fact that the material used for filling the cavity is mainly calcium hydroxide, which produces a strong alkaline reaction which can even intensify the pain. Moreover, the lactic acid produced by the bacteria continues to act and can even react by dissolving a significant amount of the filler or of the rest of the dentin. Finally, the usual fillers can give rise to thermal sensations (differences between cold and heat) or electrochemical sensations (due, for example, to acids or sugars), down to near the nerve, thereby causing discomfort. In any case, one of the greatest problems of deep caries is the possibility of bacterial infection of the pulp (pulpitis), which is very complicated to treat.

OBJECTS AND SUMMARY OF THE INVENTION

The present invention provides a satisfactory solution to these problems by means of controlled release of the $Ca^{2+}$, $F^-$ and $PO_4^{3-}$ ions on the basis of a mixture of ion-exchange resins, and in molar ratio close to that of the organomineral tissue to be remineralized. In the case of the teeth, the approximate ratio is that of fluoroapatite ($Ca_2FPO_4$), which is practically the same as in dentin. Control of release is implemented by mixing of slow-release resins (the ones of weak acid and weak base type) and fast-release resins (ones of strong acid and strong base type). Placed in contact with this mixture of resins, which is generally triturated in the form of mixture of granules (mixed beds), the organomineral tissues are remineralized in a surprisingly fast and effective way, especially if they are in the presence of $Zn^{2+}$ ions.

Thus, one of the objects of the present invention is an organomineral tissue remineralizing material which, together with other accessory components and a sufficient quantity of water, physiological serum or artificial saliva to lend it the desired texture or pastiness, comprises a mixture of ion-exchange resins, cationic and anionic, charged with the cations and anions corresponding to the salts making up the organomineral tissue to be remineralized; These ions are in a molar ratio close to that corresponding to said tissue.

DETAILED DESCRIPTION OF THE INVENTION

A preferred embodiment of the present invention is one in which the organomineral tissue to be regenerated is the dentin of human or animal teeth, in which the corresponding cations and anions are $Ca^{2+}$, $F^-$ and $PO_4^{3-}$, and the approximate molar ratio between them is 2:1:1, respectively. Particularly preferred is a material in which the resins also have a charge of $ZN^{2+}$ ions representing a proportion lower than 1%, preferably close to 0.2%, of the dry weight of the resin. The zinc has a dual effect: on the one hand it is bactericidal, thereby helping to combat the micro-organisms which cause caries, and on the other hand it acts as an initiator or catalyst suitable for stimulating ionic release of the other structural ions.

Ion-exchange resins of any type known in the art can be used, such as the acrylic resins, though the ones preferred are those whose base is cross-linked polystyrene with 2–14% divinylbenzene.

It is advisable for the mixture of resins to include both cationic resins of weak acid character (functionalized with carboxylic acid groups and resins of strong acid character (functionalized with sulphonic acid groups). Similarly, it is also advisable for the mixture of resins to include both anionic resins of weak base character (functionalized with protonated tertiary amino groups) and anionic resins of strong base character (functionalized with quaternary ammonium groups).

The most suitable way of charging the $Ca^{2+}$, $F^-$ and $PO_4^{3-}$ ions in the resins is by in-column treatment of resins in their NaCl form, with aqueous solutions of $CaCl_2$, NaF and $Na_3PO_4$, respectively. To charge the $Zn^{2+}$ ion, it is advisable to use an aqueous solution of ZnCl.

A further object of the present invention is to provide a procedure for preparing organomineral tissue remineralizing material, characterized by succession of the following stages:

i) The desired quantities of suitably functionalized commercially available ion-exchange resins (anionic or cationic) are placed in columns;

ii) The resins are purified by washings with water and with a suitable organic solvent, preferably ethanol;

iii) The acid or base forms ($H^+$ or $OH^-$) of the resins are converted into the corresponding $Na^+$ or $Cl^-$ forms, respectively, by treatments with NaCl (aq);

iv) The resins obtained in (iii) are treated with aqueous solutions of the corresponding salts: $CaCl_2$ for introducing $Ca^{2+}$ ions, $Na_3PO_4$ for introducing $PO_4^{3-}$ ions, ZnCl for introducing $Zn^{2+}$ ions, and NaF for introducing $F^-$ ions;

v) Excessive amounts of electrolyte are removed by washings with water;

vi) The resins are extracted from the columns, dried to ambient humidity conditions, and then pulverized; and vii) The different resins are mixed to obtain the desired relative charges of the various ions.

Particularly preferred is the material described in Example 1 and the utilisation methodology described in Example 2. As illustrated in Example 2, the material object of the present invention is useful for preparing a composition for the treatment of teeth with caries, particularly with deep caries. Compared with the conventional material based on calcium hydroxide which is used for the first coating of the bottom of the cavity associated with caries, the material of the present invention has the advantage of not producing overcalcification, that is, of not producing a mineral deposit with a Ca/P ratio significantly higher than the value for a normal tooth. This overcalcification has been found to be associated with a passive mineralization which involves regressive changes in the pulp, e.g. sclerosis. Moreover, as is illustrated in Example 3, the microhardness of the bottom of the cavity following treatment with the material of the present invention is greater than following the conventional treatment of deep caries, which means an additional advantage.

The advantages of the material of the present invention show themselves above all in the treatment of deep caries, in which the nature of the first coating put in place is essential. An unsatisfactory first coating means that, even if the cavity is well covered by a secondary coating (phosphate cement) or a tertiary coating (silica, metals), the thermal or electrochemical changes which cause pain still reach down close to the nerve.

The advantages of the material of the present invention can be summarized thus: it produces practically complete remineralization of the dentin within a period of 3 to 5 weeks; it produces a prolonged action in the treatment leading to the formation of a film of calcium fluorophosphate on the interior surface of the cavity, of similar microhardness and morphology to those of the original dentin; it prevents painful reactions to cold/heat and to irritating substances such as acids or sweets; it more than doubles the speed of restoration of the functional capacity of the pulp; it prevents sclerosis of the gums by eliminating excessive calcinization of the predentin material; and it prevents penetration of microflora through the bottom of the caries cavity.

The material object of the present invention can be used for the preparation of any type of dentifrice products or products for improving dental health, such as pastes, elixirs, chewing gum or dental floss. Owing to its effect against caries and its remineralization effect in the zone of the tooth in contact with the gums, the material is also beneficial in the preventive or symptomatic treatment of other related mouth infections such as gingivitis.

The material can also be used in the preparation of a composition for the treatment of damaged bones, as in the case of fractured, demineralized or aged bones. In such cases the ionic charge of the resin mixture will have to be adjusted to the composition of the bones.

The examples, which follow, illustrate the present invention in a non-restrictive way.

EXAMPLES

Example 1

General Procedure for Preparing the Remineralizing Material

Weighed quantities of commercial (LEWATIT® brand, from Bayer) ion-exchange resins (anionic or cationic), of pharmaceutical quality, based on cross-linked polystyrene with divinylbenzene (2–14%) and suitably functionalized, were used.

The cationic resins used were of two types: of weak acid character (functionalized with carboxylic groups, LEWATIT® R-250) and strong acid character (functionalized with sulphonic groups, LEWATIT® S-100).

The anionic resins used were of two types: of weak base character (functionalized with protonated tertiary amino groups, LEWATIT® MP-62) and of strong base character (functionalized with quaternary ammonia groups, LEWATIT® LM-600).

The resins were placed in columns, in which the following treatments were carried out:

a) Purification of the resin: the resin was washed three times, sequentially with deionized water and ethanol.

b) Adjusting the resin: the acid or base form ($H^+$ or $OH^-$) was converted into the corresponding $Na^+$ or $Cl^-$ form, respectively, by treatment with NaCl (aq).

c) Transformation into the desired ionic form: the resin obtained in (b) was treated with 0.2 M solutions of the corresponding salts, of analytical purity: $CaCl_2$ for introducing $Ca^{2+}$ ions, $Na_3PO_4$ for introducing $PO_4^{3-}$ ions, ZnCl for introducing $Zn^{2+}$ ions, and NaF for introducing $F^-$ ions. At the end of the treatment the quantity of ions fixed in each resin was determined by appropriate analysis of the final solution.

d) Final treatment: this consisted in washing the excess electrolyte with deionized water, removal of the resin from the column, drying to ambient humidity conditions, pulverization of the material and storage in hermetically sealed phials.

e) Mixing of the different resins: by suitable combinations of the initial resins and the salts $CaCl_2$, $ZnCl_2$, $Na_3PO_4$ and NaF, eight types of charged resins were obtained, for which the quantity of fixed ions per unit of resin mass was known. The ratio of masses of the various ions in the mixture was finally chosen to be 6.7 $Ca^{2+}$: 7.3 $PO_4^{3-}$: 7.6 $F^-$, which is the ratio corresponding to the stoichiometry of calcium fluorophosphate ($Ca_2FPO_4$). The mass of Zn was chosen so as to represent 0.2% of the total mass of the resin mixture.

Example 2

Comparative Test of Efficacy in the Regeneration of Dentin After Provoking Caries in Monkeys A total of 27 monkeys were chosen, with ages ranging between 3.5 and 4 years, weights between 3.0 and 3.5 kg. The molar and premolar teeth were chosen for carrying out the in vivo tests. Following anaesthesia of the monkeys, deep cavities were made in the vestibular surfaces of the necks of the teeth chosen. The cavities were treated with physiological solution and dried with hot air. The filling technique was the conventional one used for making dental fillings. The total number of monkeys was divided into three groups, whose cavities were treated with three different fillers. In Group 1 (control group) the bottoms of the cavities were covered with a film of asbestos (which functions as an absolutely inert material). In Group 2 calmecin (a standard filler based on calcium hydroxide) was used. In Group 3, the remineralizing system described in Example 1 was used. In order to prepare the paste which was introduced in Group 3, the powdered material whose preparation is described in Example 1 was kept beforehand in physiological solution for 1–2 min. Once the bottom of the cavities was covered with the above-mentioned films, all of them were covered conventionally: first with a phosphate cement, and then with STILIDONT® (the standard silica-based filler).

The teeth were extracted 3 or 6 months following the treatment. The extracted teeth were fixed (by means of the standard method of immersion in formaldehyde), dried, sectioned, polished, and the mineral composition (Ca and P) thereof by zone electron spectroscopy microanalysis, using Stereoscan-150 linked system-860 (US) equipment. For each tooth the composition was determined in three zones: in a central zone of the body of the tooth (central dentin), in a zone 0.1–0.2 mm from the edge of the cavity (edge dentin), and in a zone 0.5–0.7 mm away from the bottom of the cavity bottom dentin).

TABLE 1

Mineral composition (% mass) of the dentin in teeth of green monkeys, with three different materials

| Study Object | Time (months) | Elem. | Central Dentin | Edge Dentin | Bottom Dentin |
|---|---|---|---|---|---|
| Initial normal tooth | 0 | Ca | 38.3 | 37.9 | 38.2 |
| | | P | 17.3 | 17.9 | 17.4 |
| | | Ca/P | 2.2 | 2.1 | 2.2 |
| Group 1 | 3 | Ca | 38.9 | 38.6 | 34.1 |
| | | P | 17.6 | 17.6 | 17.3 |
| | | Ca/P | 2.2 | 2.1 | 2.0 |
| | 6 | Ca | 34.6 | 32.5 | 31.5 |
| | | P | 17.6 | 18.1 | 17.8 |
| | | Ca/P | 2.0 | 1.8 | 1.8 |
| Group 2 | 3 | Ca | 37.6 | 38.7 | 39.6 |
| | | P | 18.3 | 17.5 | 16.6 |
| | | Ca/P | 2.0 | 2.2 | 2.4 |
| | 6 | Ca | 39.0 | 39.2 | 42.1 |
| | | P | 16.8 | 16.7 | 13.7 |
| | | Ca/P | 2.3 | 2.3 | 2.3 |
| Group 3 | 3 | Ca | 38.5 | 37.9 | 37.9 |
| | | P | 17.8 | 18.2 | 18.3 |
| | | Ca/P | 2.2 | 2.1 | 2.1 |
| | | Ca | 37.9 | 37.9 | 37.4 |
| | | P | 18.3 | 18.3 | 18.7 |
| | | Ca/P | 2.1 | 2.1 | 2.0 |

Table 1 shows the analytical results obtained (percentage by mass), together with the Ca/P proportion calculated. The most significant results arose in the bottom dentin zone, the only one discussed here.

The results with Group 1 illustrate the behaviour of a tooth in a normal caries process: the Ca/P ratio of the bottom dentin diminishes from 2.2 (initial normal tooth) to 1.8 after 6 months, indicating that decalcification has taken place.

The results with Group 2 illustrate that, with the standard calcium hydroxide filler, the dentin undergoes overcalcification: the Ca/P ratio changes from 2.2 (initial normal tooth) to 3.2 after 6 months. Morphological studies of the final teeth have shown that what occurs is a passive overcalcification of the tissue of the dentin involving regressive changes in the pulp (e.g. sclerosis), with negative effects.

The results of Group 3 illustrate that, with the filler object of the present invention, the composition of the dentin is not significantly different between the beginning and end of the treatment of caries, which indicates that suitable remineralization of the dentin tissue has taken place and means in practice a regeneration of the dentin.

Example 3
Comparative Study of Microhardness Following Treatment of Caries in Monkeys Another group of monkeys was submitted to a treatment similar to that of Example 2 in order to determine the microhardness of the bottom dentin, using a conventional technique. The results obtained are shown in Table 2. The microhardness of the control (40 kg/mm2 in an initial normal tooth) is that corresponding to the central dentin. The results of Group 3 show that with use of the filler material of Example 1 the microhardness of the bottom of the cavity is the highest of all and that it presents the fastest growth rate at the beginning of the treatment.

TABLE 2

Microhardness of the bottom of the cavity following treatment of deep caries in monkeys

| Study object | Time (months) | Microhardness (kg/mm$^2$) |
|---|---|---|
| Normal tooth | — | 40 |
| Untreated caries | 3.5 | 29 |
| | 6.0 | 23 |
| Group 1 | 2.5 | 31 |
| | 3.5 | 50 |
| | 6.0 | 50 |
| Group 2 | 2.5 | 52 |
| | 3.5 | 64 |
| | 6.0 | 61 |
| Group 3 | 2.5 | 57 |
| | 3.5 | 67 |
| | 6.0 | 60 |

What is claimed is:

1. Organomineral tissue remineraling material which comprises a mixture of cationic and anionic ion-exchange resins, characterized in that, together with other accessory components and a sufficient quantity of water, physiological serum or artificial saliva to lend it the desired texture or pastiness, said mixture of resins includes at least one of cationic resins of weak acid character which is only partially dissociated in aqueous solution and cationic resins of strong acid character, and at least one of anionic resins of weak basic character which is only partially dissociated in aqueous solution and anionic resins of strong basic character, said mixture of resins being charged with the cations and anions corresponding to the mineral compounds making up the organomineral tissue to be remineralized, said ions being in a molar ratio close to that corresponding to said tissue.

2. Material as claimed in claim 1, characterized in that the organomineral tissue to be regenerated is the dentin of human or animal teeth, and in that the corresponding cations and anions are $Ca^{2+}$, $F^-$ and $PO_4^{3-}$, and the approximate molar ratio between them is 2:1:1, respectively.

3. Material as claimed in claim 1, characterized in that the resins also have a charge of $ZN^{2+}$ ions representing a proportion lower than 1% of the dry weight of the resin.

4. Material as claimed in claim 1, characterized in that the base of the resins is cross-linked polystyrene with 2–14% divinylbenzene.

5. Material as claimed in claim 1, characterized in that the mixture of resins includes cationic resins functionalized with carboxylic acid groups.

6. Material as claimed in claim 1, characterized in that the mixture of resins includes resins functionalized with sulphonic acid groups.

7. Material as claimed in claim 1, characterized in that the mixture of resins includes anionic resins functionalized with protonated tertiary amino groups.

8. Material as claimed in claim 1, characterized in that the mixture of resins includes anionic resins functionalized with quaternary ammonium groups.

9. Material as claimed in claim 2, characterized in that the $Ca^{2+}$, $F^-$ and $PO_4^{3-}$ ions are charged by treatment of the resins in their NaCl form with aqueous solutions of $CaCl_2$, NaF and $Na_3PO_4$, respectively.

10. Material as claimed in claim 3, characterized in that the proportion of $Zn^{2+}$ is approximately 0.2%.

11. Organomineral tissue remineralizing material as claimed in claim 10, characterized in that the $Zn^{2+}$ ion is charged by treating resins in their NaCl form with aqueous solutions of ZnCl.

12. Procedure for the preparation of the material of claim 1, characterized by succession of the following stages:
   i) The desired quantities of suitably functionalized commercially available ion-exchange resins (anionic or cationic) are placed in columns; they are purified by washings with water and with a suitable organic solvent;
   ii) The acid or base forms ($H^+$ or $OH^-$) of the resins are converted into the corresponding $Na^+$ or $Cl^-$ forms, respectively, by treatments with NaCl (aq);
   iii) The resins obtained in (ii) are treated with aqueous solutions of the corresponding salts: $CaCl_2$ for introducing $Ca^{2+}$ ions, $Na_3PO^4$ for introducing $PO_4^{3-}$ ions, ZnCl for introducing $Zn^{2+}$ ions, and NaF for introducing $F^-$ ions; and excessive amounts of electrolyte are removed by washings with water;
   iv) The resins are extracted from the columns, dried to ambient humidity conditions, and then pulverized; and
   v) The different resins are mixed to obtain a final ratio of masses of the various ions in the mixture of resins 6.7 $Ca^{2+}$:7.3 $PO_4^{3-}$:7.6 $F^-$ and a mass of $Zn^{2-}$ that represents the 0.2% of total mass of the resin mixture.

13. A composition for remineralizing organomineral tissue comprising:
   a first ion-exchange resin charged with $Ca^{2+}$ cations; and
   a second ion-exchange resin charged with $F^-$ and $PO_4^{3-}$ anions, the molar ratio of $Ca^{2+}$ to $F^-$ to $PO_4^{3-}$ being 2:1:1.

14. The composition as claimed in claim 13, wherein said cations and said anions each have a molar ratio substantially similar to a molar ratio of the organomineral tissue to be remineralized.

15. The composition of claim 13, wherein said organomineral tissue to be remineralized is the dentin of human or animal teeth and wherein said cations are selected from the group consisting of calcium and zinc, and wherein said anions are selected from the group consisting of fluoride and phosphate.

16. The composition as claimed in claim 13, wherein said resins further comprise a base that is cross linked polystyrene with about 2–14% divinylbenzene.

17. The composition as claimed in claim 13, wherein said resins are treated with an aqueous solution selected from the group consisting of $CaCl_2$, NaF, $Na_3PO_4$ and ZnCl.

18. A method of remineralizing a mammalian tooth containing dental caries, comprising applying a sufficient amount of the composition of claim 1 to the affected surface of a mammalian tooth containing dental caries.

19. A dentifrice comprising the material of claim 1.

20. A composition for treating damaged bones, comprising a sufficient amount of the material of claim 1.

21. An organomineral tissue remineraling material which comprises a mixture of cationic and anionic ion-exchange resins, characterized in that, together with other accessory components and a sufficient quantity of water, physiological serum or artificial saliva to lend it the desired texture or pastiness, said mixture of resins further comprising at least one of cationic resins of weak acid character which is only partially dissociated in aqueous solution and cationic resins of strong acid character, and at least one of anionic resins of weak basic character which is only partially dissociated in aqueous solution and anionic resins of strong basic character, said mixture of resins charged with the cations corresponding to the mineral compounds making up the organomineral tissue to be remineralized, and said cations and said anions being in a molar ratio close to that corresponding to said organomineral tissue.

* * * * *

UNITED STATES PATENT AND TRADEMARK OFFICE
CERTIFICATE OF CORRECTION

PATENT NO.    : 6,413,498 B1
DATED         : July 2, 2002
INVENTOR(S)   : Valiente Malmagro et al.

It is certified that error appears in the above-identified patent and that said Letters Patent is hereby corrected as shown below:

Title page,
Item [22], the PCT Filed date should be added as -- December 30, 1997 --
Item [86], the PCT number should be added as -- PCT/ES97/00316 -- the 371 date should be added as -- July 6, 1999 --
Item [87], the PCT Publication Number should be added as -- WO98/30191 -- the PCT Publication Date should be added as -- July 16, 1998 --
Item [30], the Foreign Application Priority Data should be added as
-- Jan. 7, 1997 (ES)....................9700016 --

Signed and Sealed this

Twenty-fifth Day of March, 2003

JAMES E. ROGAN
*Director of the United States Patent and Trademark Office*